United States Patent
Krishna et al.

(10) Patent No.: US 12,340,312 B2
(45) Date of Patent: *Jun. 24, 2025

(54) SYSTEMS AND METHODS FOR AUTOMATIC DETECTION OF SURGICAL SPECIALTY TYPE AND PROCEDURE TYPE

(71) Applicant: Stryker Corporation, Kalamazoo, MI (US)

(72) Inventors: Kundan Krishna, Surrey (CA); Amit A. Mahadik, San Jose, CA (US); Hannes Rau, Milpitas, CA (US)

(73) Assignee: Stryker Corporation, Portage, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/636,184

(22) Filed: Apr. 15, 2024

(65) Prior Publication Data

US 2024/0265259 A1   Aug. 8, 2024

Related U.S. Application Data

(63) Continuation of application No. 17/189,072, filed on Mar. 1, 2021, now Pat. No. 11,960,995.
(Continued)

(51) Int. Cl.
*G06N 3/08* (2023.01)
*G06F 18/214* (2023.01)
(Continued)

(52) U.S. Cl.
CPC ............ *G06N 3/08* (2013.01); *G06F 18/214* (2023.01); *G06F 18/2431* (2023.01);
(Continued)

(58) Field of Classification Search
None
See application file for complete search history.

(56) References Cited

U.S. PATENT DOCUMENTS 9,171,477 B2   10/2015   Luo et al.
11,189,379 B2 *   11/2021   Giataganas ............ G16H 10/60
(Continued)

FOREIGN PATENT DOCUMENTS

EP   3537448 A1   9/2019
WO   2020/023740 A1   1/2020

OTHER PUBLICATIONS

International Preliminary Report on Patentability dated Sep. 6, 2022, directed to International Application No. PCT/US2021/020317; 8 pages.
(Continued)

*Primary Examiner* — Soo Shin
(74) *Attorney, Agent, or Firm* — Morrison & Foerster LLP

(57) ABSTRACT

Systems and methods for automatic detection of surgical specialty type and procedure type are disclosed. One or more classification networks may be applied to automatically process input surgical image data in order to recognize and determine a surgical specialty type and a surgical procedure type depicted in the input image data. Based on the determination made by the system, one or more output indications may be generated and one or more surgical devices may be automatically controlled, such as by being optimized for use during the surgical procedure type and/or surgical specialty type represented by the input image.

20 Claims, 5 Drawing Sheets

Related U.S. Application Data

(60) Provisional application No. 62/985,806, filed on Mar. 5, 2020.

(51) Int. Cl.

| | |
|---|---|
| *G06F 18/2431* | (2023.01) |
| *G06V 10/44* | (2022.01) |
| *G06V 10/764* | (2022.01) |
| *G06V 10/77* | (2022.01) |
| *G06V 20/52* | (2022.01) |
| *G06V 40/60* | (2022.01) |
| *G16H 20/40* | (2018.01) |
| *G16H 30/20* | (2018.01) |
| *G16H 30/40* | (2018.01) |
| *G16H 40/60* | (2018.01) |

(52) U.S. Cl.
CPC .......... *G06V 10/454* (2022.01); *G06V 10/764* (2022.01); *G06V 10/7715* (2022.01); *G06V 20/52* (2022.01); *G06V 40/67* (2022.01); *G16H 20/40* (2018.01); *G16H 30/20* (2018.01); *G16H 30/40* (2018.01); *G16H 40/60* (2018.01)

(56) References Cited

U.S. PATENT DOCUMENTS

| | | | | |
|---|---|---|---|---|
| 11,960,995 | B2* | 4/2024 | Krishna | G06N 3/08 |
| 2018/0357514 | A1* | 12/2018 | Zisimopoulos | G06V 10/764 |
| 2021/0279464 | A1* | 9/2021 | Krishna | G16H 30/40 |
| 2021/0307841 | A1* | 10/2021 | Buch | A61B 5/749 |
| 2021/0366125 | A1* | 11/2021 | Jia | G06F 18/211 |
| 2022/0265121 | A1* | 8/2022 | Fouts | A61B 1/317 |

OTHER PUBLICATIONS

International Search Report and Written Opinion mailed May 20, 2021, directed to International Application No. PCT/US2021/020317; 14 pages.

Krishna et al., U.S. Notice of Allowance and Fee(s) Due mailed Dec. 15, 2023, directed to U.S. Appl. No. 17/189,072; 7 pages.

Krishna et al., U.S. Office Action dated Jul. 5, 2023, directed to U.S. Appl. No. 17/189,072; 19 pages.

Examination Report mailed Jun. 25, 2024, directed to EP Application No. 21713842.9; 6 pages.

* cited by examiner

SYSTEMS AND METHODS FOR AUTOMATIC DETECTION OF SURGICAL SPECIALTY TYPE AND PROCEDURE TYPE

CROSS-REFERENCE TO RELATED APPLICATIONS

This application is a continuation of U.S. patent application Ser. No. 17/189,072, filed Mar. 1, 2021, which issued as U.S. Pat. No. 11,960,995, which claims benefit of U.S. Provisional Application No. 62/985,806, filed Mar. 5, 2020, the contents of each of which is incorporated herein by reference in its entirety.

FIELD

The present disclosure relates generally to surgical procedures, and more specifically systems and methods for automatic detection of surgical specialty type and procedure type using image analysis.

BACKGROUND

Surgical specialty and procedure type information are important inputs for minimally invasive surgery (MIS) and for other surgical operation. In some embodiments, this information may be used to configure surgical devices for optimal operation with the indicated surgical specialty type and/or procedure type. This information may assist in achieving the overall quality of the surgical outcome. According to known techniques, surgical specialty information, procedure type information, and/or procedure step information is manually indicated by a user (e.g., surgeon) of surgical equipment.

SUMMARY

As explained above, according to known techniques, surgical specialty information, procedure type information, and/or procedure step information is manually indicated by a user (e.g., surgeon) of surgical equipment. However, manual indication of surgical specialty information, procedure type information, and/or procedure step information may be time-consuming, inaccurate, and prone to user error or accidental omission. Accordingly, there is a need for methods for automated, accurate, and reliable determination of surgical specialty information, procedure type information, and/or procedure step information.

Disclosed herein are systems, methods, and techniques for automatically detecting and classifying surgical specialty type and procedure type using image analysis. As explained herein, one or more classification networks may be applied to automatically process input surgical image data in order to recognize and determine a surgical specialty type and a surgical procedure type depicted in the input image. Based on the determination made by the system, one or more output indications may be generated and one or more surgical devices may be automatically controlled, such as by being optimized for use during the surgical procedure type and/or surgical specialty type represented by the input image.

Use of the systems, methods, and techniques described herein during surgical procedures (e.g., endoscopic, other minimally invasive, or non-invasive surgical procedures) may allow medical systems to automatically and quickly determine a surgical specialty type, procedure, and/or step of an ongoing procedure based on video and/or images of the ongoing procedure and without manual or explicit input. Furthermore, the systems described herein can automatically optimize the usage of one or more medical and/or other devices based on the determined surgical specialty type, procedure, and/or step, such as by automatically optimally configuring illumination and/or image-capture devices for the detected specialty, procedure, and/or step.

According to an aspect, a first surgical system is provided, the first surgical system comprising: one or more processors configured to: receive image data representing a surgical environment; process the image data using a first classification network to generate first classification output data indicating a determined surgical specialty type represented by the image data of the surgical environment; in accordance with the first classification output data indicating the determined surgical specialty type, select a second classification network from a first plurality of classification networks; process the image data using the second classification network to generate second classification output data indicating a determined procedure type represented by the image data of the surgical environment.

Optionally, the first classification network is trained using a first set of training image data; and the second classification network is trained using a second set of training image data.

Optionally, the second set of training image data is a subset of the first set of training image data.

Optionally, the first classification network and the second classification network are both trained using a same set of training image data.

Optionally, one or more of the first classification network and the second classification network comprises a convolutional neural network comprising a plurality of convolution layers and a plurality of fully-connected layers.

Optionally: the fully-connected layers are configured in accordance with a set of training image data comprising surgical images labeled with one or both of surgical specialty type metadata and procedure type metadata; and the convolution layers are configured without reference to the set of training image data.

Optionally, the one or more processors are further configured to: in accordance with the second classification output data indicating the determined procedure type, select a third classification network from a second plurality of classification networks; process the image data using the third classification network to generate third classification output data indicating a determined procedure step represented by the image data of the surgical environment.

Optionally, the first surgical system further comprises a surgical device configured to be automatically changed between activation states, wherein the one or more processors are further configured to: based on one or more of the first classification output and the second classification output data, automatically change an activation state of the surgical device.

Optionally, automatically changing the activation state of the surgical device based on one or more of the first classification output and the second classification output comprises: if a first set of one or more predefined criteria are satisfied by the first classification output, automatically changing the activation state; and if a second set of one or more predefined criteria, different from the first set of one or more predefined criteria, are satisfied by the second classification output, automatically changing the activation state.

Optionally: the first set of one or more predefined criteria comprise that the determined surgical specialty type has been indicated by data received by the system for a first predefined minimum amount of time; and the second set of one or more predefined criteria comprise that the determined procedure type has been indicated by data received by the system for a second predefined minimum amount of time.

Optionally, automatically changing the activation state of the surgical device comprises performing an operation selected from turning the device on and turning the device off.

Optionally, automatically changing the activation state of the surgical device comprises changing a setting of the surgical device.

Optionally, the surgical device comprises an image-capture device.

Optionally, the surgical device comprises an illumination device.

Optionally, the surgical device comprises an image processing system.

Optionally, the first surgical system further comprises an output device, wherein the one or more processors are further configured to: based on one or more of the first classification output and the second classification output data, automatically provide an output indication via the output device.

Optionally, the output device comprises a display and providing an output indication comprises displaying the output indication.

Optionally, receiving the image data comprises receiving the image data from an endoscopic video feed.

Optionally, the one or more processors are further configured to pre-process the image data to configure the image data to be processed by one or more of the first classification network and the second classification network.

Optionally, pre-processing the image data comprises cropping the image data.

Optionally, pre-processing the image data comprises scaling the image data.

Optionally, pre-processing the image data comprises one or more of translating, flipping, shearing, and stretching the image data.

According to an aspect, a first method performed at a surgical system comprising one or more processors is provided, the first method comprising: receiving image data representing a surgical environment; processing the image data using a first classification network to generate first classification output data indicating a determined surgical specialty type represented by the image data of the surgical environment; in accordance with the first classification output data indicating the determined surgical specialty type, selecting a second classification network from a first plurality of classification networks; and processing the image data using the second classification network to generate second classification output data indicating a determined procedure type represented by the image data of the surgical environment.

According to an aspect, a first non-transitory computer-readable storage is provided, the first non-transitory computer-readable storage medium storing instructions configured to be executed by a surgical system comprising one or more processors to cause the surgical system to: receive image data representing a surgical environment; process the image data using a first classification network to generate first classification output data indicating a determined surgical specialty type represented by the image data of the surgical environment; in accordance with the first classification output data indicating the determined surgical specialty type, select a second classification network from a first plurality of classification networks; process the image data using the second classification network to generate second classification output data indicating a determined procedure type represented by the image data of the surgical environment.

According to an aspect, a second surgical system is provided, the second surgical system comprising one or more processors configured to: receive image data representing a surgical environment; process the image data using a first classification network to generate first classification output data indicating a determined surgical specialty type represented by the image data of the surgical environment; and process the image data using a second classification network to generate second classification output data indicating a determined procedure type represented by the image data of the surgical environment.

Optionally: the first classification network is trained using a first set of training image data; and the second classification network is trained using a second set of training image data.

Optionally, the second set of training image data is a subset of the first set of training image data.

Optionally, the first classification network and the second classification network are both trained using a same set of training image data.

Optionally, the first classification network comprises a first convolutional neural network comprising a first plurality of convolution layers and a first plurality of fully-connected layers; and the first classification network comprises a second convolutional neural network comprising a second plurality of convolution layers and a second plurality of fully-connected layers.

Optionally: the first plurality of fully-connected layers are configured in accordance with training image data comprising surgical specialty type metadata; and the second plurality of fully-connected layers are configured in accordance with training image data comprising procedure type metadata.

Optionally, the surgical specialty type metadata and the procedure type metadata comprise labels for one or more common images in the training image data.

According to an aspect, a second method performed by a surgical system comprising one or more processors is provided, the second method comprising: receiving image data representing a surgical environment; processing the image data using a first classification network to generate first classification output data indicating a determined surgical specialty type represented by the image data of the surgical environment; and processing the image data using a second classification network to generate second classification output data indicating a determined procedure type represented by the image data of the surgical environment.

According to an aspect, a second non-transitory computer-readable storage medium is provided, the second non-transitory computer-readable storage medium storing instructions configured to be executed by a surgical system comprising one or more processors and to cause the surgical system to: receive image data representing a surgical environment; process the image data using a first classification network to generate first classification output data indicating a determined surgical specialty type represented by the image data of the surgical environment; and process the image data using a second classification network to generate second classification output data indicating a determined procedure type represented by the image data of the surgical environment.

According to an aspect, a third surgical system is provided, the third surgical system comprising: receive image data representing a surgical environment; process the image data using a classification network to generate first classification output data indicating a determined procedure type represented by the image data of the surgical environment; and based on the determined procedure type, generate second classification output data indicating a surgical specialty type of the surgical environment.

Optionally, generating the second classification output data comprises determining that the determined surgical specialty type corresponds to the determined procedure type.

Optionally, determining that the determined surgical specialty type corresponds to the determined procedure type is performed using one or more of a lookup table, an index, or a database comprising information regarding correspondence between surgical specialty types and procedure types.

According to an aspect, a third method performed by a surgical system comprising one or more processors is provided, the third method comprising: receiving image data representing a surgical environment; processing the image data using a classification network to generate first classification output data indicating a determined procedure type represented by the image data of the surgical environment; and based on the determined procedure type, generating second classification output data indicating a surgical specialty type of the surgical environment.

According to an aspect, a third non-transitory computer-readable storage medium is provided, the third non-transitory computer-readable storage medium storing instructions configured to be executed by a surgical system comprising one or more processors and to cause the surgical system to: receive image data representing a surgical environment; process the image data using a classification network to generate first classification output data indicating a determined procedure type represented by the image data of the surgical environment; and based on the determined procedure type, generate second classification output data indicating a surgical specialty type of the surgical environment.

It will be appreciated that any of the aspects, features and options described in view of the system(s) apply equally to the method(s) and computer-readable storage medium(s), and vice versa. It will also be clear that any one or more of the above aspects, features and options can be combined. According to an aspect, any one or more of the characteristics of any one or more of the systems, methods, and/or computer-readable storage mediums recited above may be combined, in whole or in part, with one another and/or with any other features or characteristics described elsewhere herein.

BRIEF DESCRIPTION OF THE FIGURES

Features will become apparent to those of ordinary skill in the art by describing in detail exemplary embodiments with reference to the attached drawings in which.

DETAILED DESCRIPTION

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

As explained in detail below, this disclosure sets forth systems, methods, and techniques for automatic detection of surgical specialty type and procedure type, and in some embodiments automatic detection of procedure step. As explained below, the techniques set out herein may apply image analysis techniques to automatically detect a surgical specialty type, a procedure type, and/or a procedure step based on one or more images of a surgery and/or surgical environment. As used herein, surgical specialty type may refer to a class of surgical procedures grouped according to a common specialty type. For example, specialty types may include laparoscopic specialty type and arthroscopic specialty type. As used herein, procedure type may refer to a specific type of surgical procedure, such as LAP Cholecystectomy (a surgical procedure type falling within the laparoscopic specialty type) and right ACL reconstruction (a surgical procedure type falling within the arthroscopic specialty type). Surgical procedure type may thus be a narrower classification than surgical specialty type. As used herein, procedure step may refer to a specific step of surgical procedure, such as (for LAP Cholecystectomy): endoscope insertion, cavity inspection, lysing of filmy adhesions, exposure of Calot's triangle, dissection of peritoneum, separation of peritoneal attachments, and removal of gallbladder; or (for right ACL reconstruction), endoscope insertion, harvest, cleanup, notch, tunnels, and insert. Surgical procedure step may thus be a narrower classification than surgical procedure type. In some embodiments, one or more of the classification types listed above may nest within one of the other classification types; for example, a surgical specialty type may encompass multiple different surgical procedure types, and a surgical procedure type may include multiple different procedure steps.

While the disclosure herein is set forth using examples regarding discriminating between surgical specialty types, procedure types, and procedure steps, a person of ordinary skill in the art would recognize that the disclosure herein may be similarly applied to other classifications for surgical or non-surgical imagery, including other nested classifications (including nested classifications having greater or fewer than three levels of nesting as with the specialty-procedure-step example set forth herein).

Figure 1:
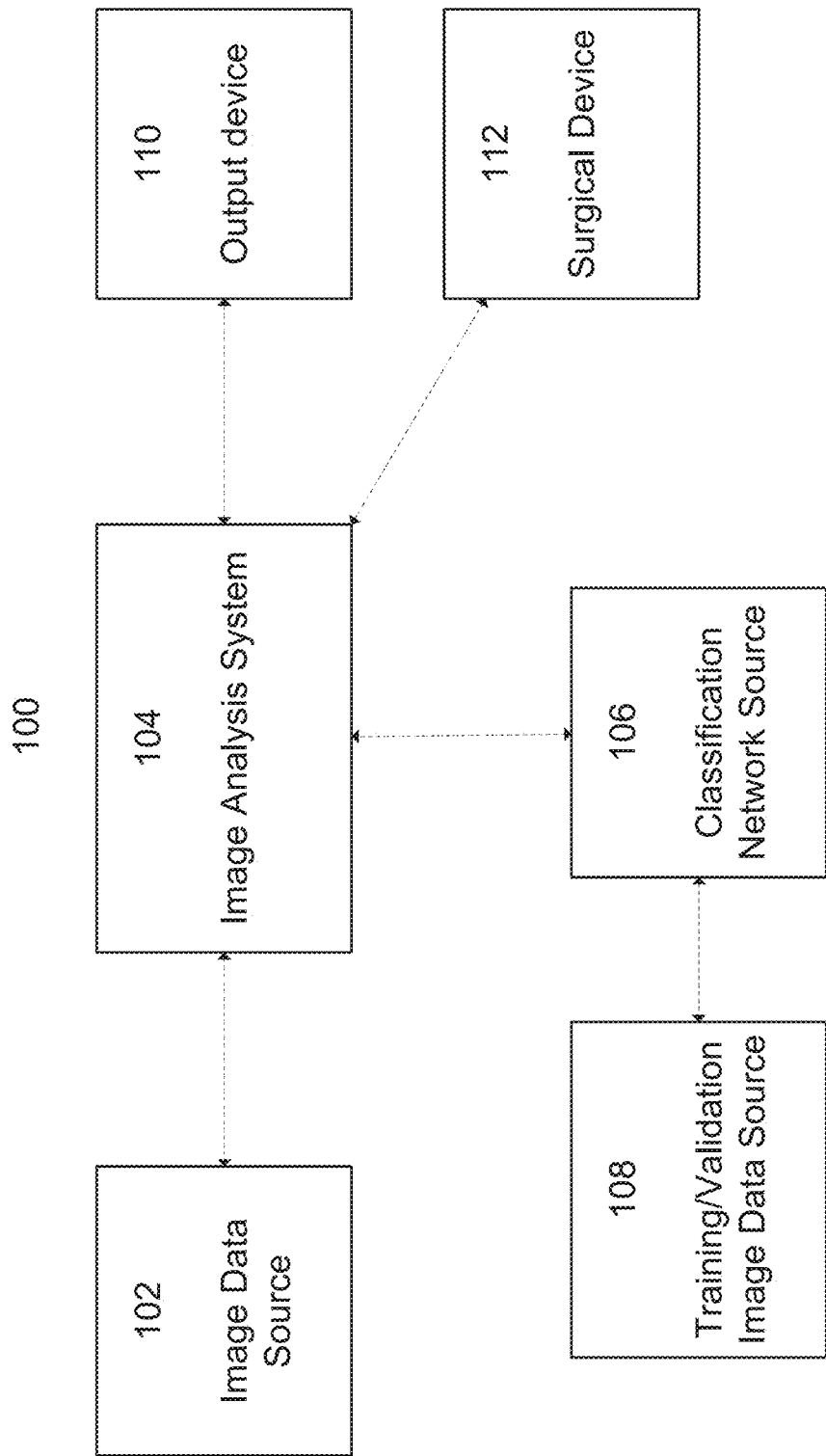
FIG. 1 depicts a system for automatic detection of surgical specialty type and procedure type, in accordance with some embodiments.

FIG. 1 depicts a system for automatic detection of surgical specialty type and procedure type, in accordance with some embodiments.

As shown, system 100 may include image data source 102, image analysis system 104, classification network source 106, training/validation image data source 108, output device 110, and surgical device 112. Each of these components may be communicatively coupled with one or more of the other components such that they may send and receive electronic information via network communication amongst one another, for example as shown by the dotted lines in FIG. 1. As shown in the example of FIG. 1, image analysis system 104 may be communicatively coupled to each one of image data source 102, classification network source 106, output device 110, and surgical device 112. As shown in the example of FIG. 1, classification network source 106 may be communicatively coupled to both image analysis system 104 and to training/validation image data source 108.

In some embodiments, image data source 102 may be any electronic source for medical or surgical images and/or video, such as an image capture device, an image-capture and/or video-capture endoscope, an image or video broadcasting or relaying device, one or more servers, and/or one or more databases or repositories. Image data source 102 may be configured to transmit image data (e.g., medical/surgical image data and/or medical/surgical video data) to image analysis system 104 by any wired or wireless electronic communication medium, including by any suitable network communication protocol.

In some embodiments, image analysis system 104 may be any device or system comprising one or more computer processors configured to receive image data, assess and/or process the received image data, and to generate and transmit one or more output signals in accordance with the results of the image assessment. In some embodiments, image analysis system 104 may be provided, in whole or in part, as all or part of a desktop computing device, laptop, tablet, mobile electronic device, dedicated medical image processing device, computing module, processor, server, cloud computing system, distributed computing system, or the like. In some embodiments, image analysis system 104 may be provided locally with respect to surgical device 112 (e.g., in the surgical suite), while in some embodiments image analysis system 104 may be provided remotely from surgical device 112 (e.g., outside the surgical suite, elsewhere in a hospital, at a remote server location, etc.).

In some embodiments, image analysis system 104 may be configured to receive image data (e.g., image and/or video data showing a surgical image) from image data source 102 and to process the image to determine a surgical specialty type, procedure type, and/or procedure step that is depicted in the image data received. In some embodiments, image analysis system 104 may be configured to determine a surgical specialty type, procedure type, and/or procedure step by analyzing the image data received from image data source 102 using one or more machine learning techniques, including by applying one or more algorithms, models, and/or classification networks to the received image data. In some embodiments, image analysis system 104 may be configured to process the received image data using one or more classification networks such as a deep neural network, convolutional neural network, or the like. In some embodiments, image analysis system 104 may be configured to determine a surgical specialty type, procedure type, and/or procedure step in accordance with one or more of the techniques discussed below with reference to FIGS. 2-4.

In some embodiments, image analysis system 104 may be configured to receive one or more classification networks from classification network source 106, wherein the one or more classification networks received may be used by image analysis system 104 to process the image data as discussed above. In some embodiments, classification network source 106 may be any electronic source for classification networks, such as one or more servers, one or more databases or repositories, and/or one or more systems configured to generate (e.g., train) one or more classification networks. Classification network source 106 may be configured to transmit classification network data (e.g., classification networks, classification network metadata, and/or one or more rules and/or policies regarding applying the one or more classification networks) to image analysis system 104 by any wired or wireless electronic communication medium, including by any suitable network communication protocol.

In some embodiments, training/validation image data source 108 may be any electronic source for medical or surgical images and/or video that may be used to train and/or validate one or more classification networks. In some embodiments, training/validation image data source may also provide metadata associated with training image data and/or validation image data, such as classification labels for labeled training image data and/or validation image data. In some embodiments, training image data source 108 may include one or more image capture or video-capture devices, one or more image or video broadcasting or relaying devices, one or more servers, and/or one or more databases or repositories. Training/validation image data source 108 may be configured to transmit training image data and/or validation image data (and any associated metadata) to image analysis system 104 by any wired or wireless electronic communication medium, including by any suitable network communication protocol.

In some embodiments, output device 110 may be configured to provide one or more output indicators based on output data received from image analysis system 104. For example, image analysis system 104 may transmit output data to output device 110, wherein the output data indicates the determined surgical specialty type, procedure type, and/or procedure step. Based on the output data received, output device 110 may then responsively provide one or more output indicators such as a visible, audible, and/or haptic indicator that may be received by a human user and/or by another electronic system. In some embodiments, output device 110 may comprise one or more display devices, illumination devices, speaker devices, and/or haptic output devices. In some embodiments, an output indicator may comprise a displayed indication of the determined surgical specialty type, procedure type, and/or procedure step. In some embodiments, output device 110 may be configured to receive output data and/or other transmissions from image analysis system 104 by any wired or wireless electronic communication medium, including by any suitable network communication protocol.

In some embodiments, image analysis system 104 may be configured to send one or more instruction or control signals to surgical device 106 configured to alter an activation state of the surgical device 106 (e.g., to turn from off to on, or to turn from on to off, and/or to change a setting or configuration of the device); in some embodiments, the instruction or control signal may be sent by image analysis system 104 in accordance with the surgical specialty type, procedure type, and/or procedure step, as determined based on analysis of the image data received. For example, in some embodiments, one or more surgical devices (such as illumination devices, image capture devices, or the like) may be turned on, turned off, and/or configured in accordance with predefined settings stored in association with the determined surgical specialty type, procedure type, and/or procedure step.

In some embodiments, surgical device 112 may be any surgical device, medical device, imaging device, or the like, that is configured to be activated and/or deactivated (or to otherwise have an activation state set or changed) in accordance with an instruction received from image analysis system 104. In some embodiments, surgical device 112 may be wholly hardware, wholly software, or may comprise both hardware and software. In some embodiments, surgical device 112 may be a physical device, such as an illumination device and/or an image capture device. In some embodiments, surgical device 112 may be a software component, such as image capturing software and/or image processing software configured to capture and/or process one or more medical images (including, for example, medical images received from image data source 102 and analyzed to determine surgical specialty type, procedure type, and/or procedure step).

As discussed above, in some embodiments, device 106 may be configured to have an activation state modified in accordance with an instruction signal or control signal received from image analysis system 104. In some embodiments, device 106 may be configured to receive instruction signals and/or control signals from image analysis system 104 by any wired or wireless electronic communication medium, including by any suitable network communication protocol.

Figure 2:
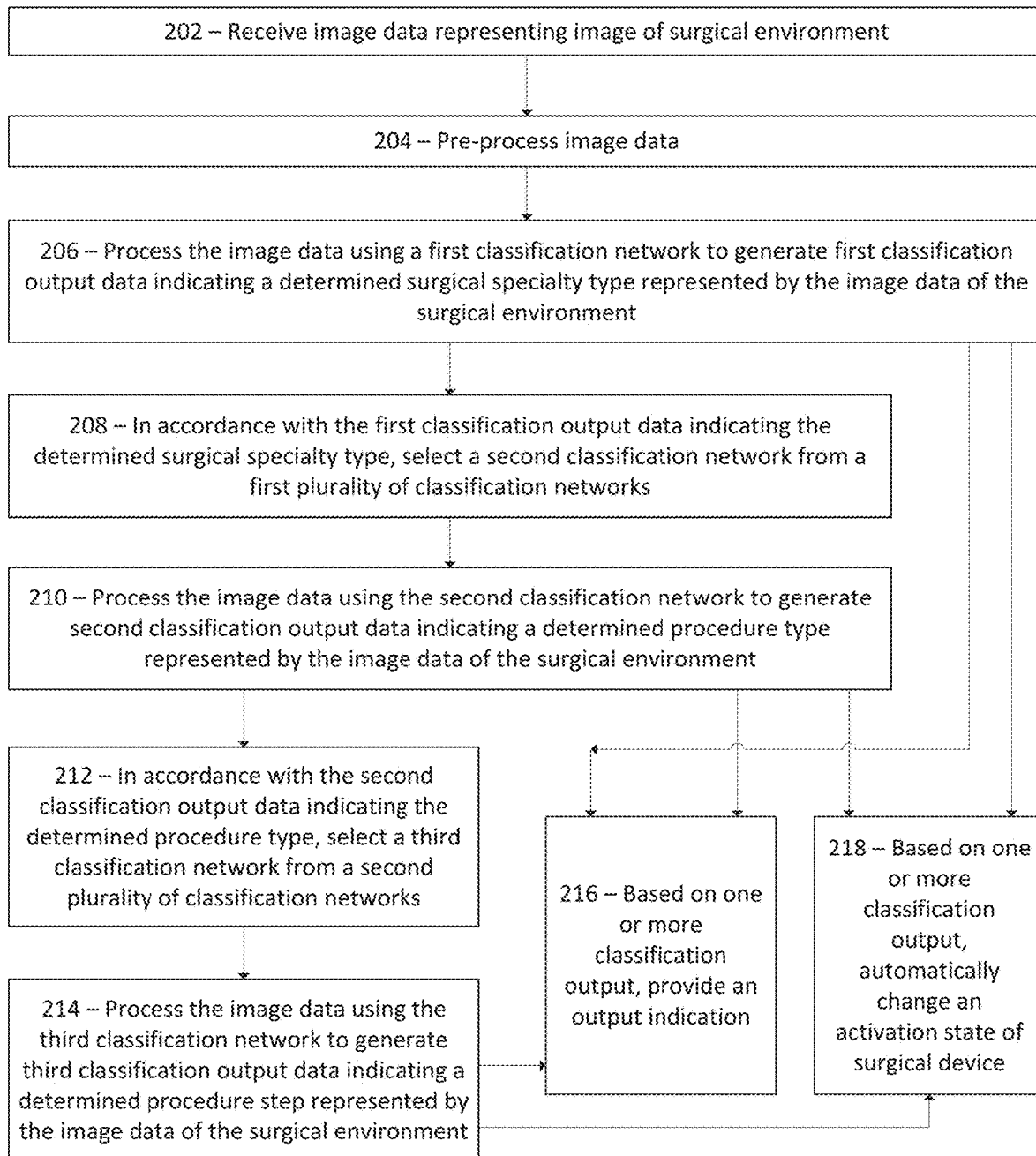
FIG. 2 depicts a flowchart representing an exemplary method for automatic detection of surgical specialty type and procedure type, in accordance with some embodiments.

FIG. 2 depicts a flowchart representing an exemplary method 200 for automatic detection of surgical specialty type and procedure type, in accordance with some embodiments. As described below in detail, method 200 may enable an image analysis system to receive surgical images or videos; to process the surgical images or videos to determine a surgical specialty type, procedure type, and/or procedure step depicted in the received images/videos; and to provide an output and/or automatically enable, disable, or configure a setting of one or more surgical devices based on the determined surgical specialty type, procedure type, and/or procedure step.

As described below, method 200 may enable a system to receive surgical image data and to first process the image data using a first classification network configured to determine a surgical specialty type represented by the image data. Based on the determined surgical specialty type, the system may then select a second classification network configured to discriminate between different procedure types that fall within the determined surgical specialty type, and may apply the selected second classification network to the received image data to determine a procedure type represented by the image data. In some embodiments, based on the determined procedure type, the system may then select a third classification network configured to discriminate between different procedure steps of the determined procedure type, and may apply the selected third classification network to the received image data to determine a procedure step represented by the image data. Based on one or more of the determined surgical specialty type, the determined procedure type, and the determined procedure step, the system may then provide one or more output indications and/or may automatically change an activation state of a surgical device.

In some embodiments, method 200 may be carried out, in whole or in part, by one or more of the components of a system for automatic detection of surgical specialty type and procedure type, such as system 100 described above with respect to FIG. 1. In some embodiments, any one or more of the aspects of method 200 may be combined, in whole or in part, with any one or more of the aspects of FIG. 1, and/or with any one or more of the systems, methods, devices, and/or techniques described elsewhere herein.

At block 202, in some embodiments, the system may receive image data representing an image of a surgical environment. In the example of system 100, image analysis system 104 may receive image data representing an image of a surgical environment from image data source 102.

The image data received by the system may be in the form of a still image or one or more frames of a video image, and may depict a surgical environment (e.g., an area in and/or near a tissue segment on which surgery is being performed) about which it is not known by the system what surgical specialty type, procedure type, or procedure step is depicted by the received image data. The image data may be received from an image or video capture device, an image or video broadcasting or relaying device, one or more servers, and/or one or more databases or repositories. The image data received may be received via any suitable form of electronic communication, including wired and/or wireless network communication.

At block 204, in some embodiments, the system may perform one or more pre-processing techniques on the received image data. In some embodiments, the system may perform any one or more data augmentation techniques on the received image data. For example, the system may perform cropping, alignment, translation, flipping, shearing, stretching, and/or re-sizing (e.g., scaling) of the received image data before additional processing steps are performed. Data pre-processing and/or data augmentation may be particularly useful when a system does not have access to large and/or highly-standardized image data sets; thus, data pre-processing and/or data augmentation may be used to make a model more generally applicable to different kinds of data sets. In some embodiments, said pre-processing may be carried out by image analysis system 104.

In some embodiments, a cropping procedure may comprise identifying a region-of-interest (ROI) in the image data received, such that additional image processing techniques such as those described below may be performed only on the ROI selected, rather than on the entire original image. In some embodiments, an ROI may be selected manually by a user of the system. In some embodiments, an ROI may be selected automatically by one or more algorithms. In some embodiments, an ROI may be selected automatically as a predefined area (e.g., a predefined rectangular area of a given image size, e.g., a given pixel size) within a field of view of the received image data. In some embodiments, an ROI may be selected automatically as a region defined by a finding circle image processing approach, in which intersection points between a scope edge and a diagonal line of an image frame are used as reference points to calculate an inner rectangle defining the ROI.

In some embodiments, an alignment procedure may comprise rotating or aligning all or part of the received image data, such that additional image processing techniques such as those described below may be performed only on the aligned image, rather than on the entire original image.

In some embodiments, a scaling procedure may comprise scaling (e.g., resizing) all or part of the received image data, such that additional image processing techniques such as those described below may be performed only on the scaled image, rather than on the entire original image. For example, an image may be reduced in size such that the reduced-size, downscaled image may be used for one or more of the image processing techniques described below, rather than the original full-size image.

In some embodiments, one or more image pre-processing techniques may configure the image data to be processed by one or more of the classification networks as discussed herein. For example, a classification network may be configured to process surgical images having a predefined size and/or resolution, or a classification network may be configured to process surgical images aligned in a certain way and/or showing certain features in a region of interest of the image.

In some embodiments, one or more image pre-processing techniques may be selected for application (e.g., selected automatically by the system and/or selected based on explicit user input) based on the classification network(s) that the system will apply to the pre-processed image (as described below). For example, metadata associated with a classification network may indicate what kinds of pre-processing procedures should be applied to image data, and the system may read that metadata and pre-process the image data in accordance therewith.

In some embodiments, more than one of the image pre-processing techniques may be performed on the same image data. For example, a single image frame may be subject to any two or more image preprocessing techniques before proceeding to the image processing techniques discussed below. In some embodiments, no image preprocessing techniques may be employed (e.g., the raw image data initially received may be used for the image processing steps described below). It should be understood that when this disclosure refers to processing image data in method 200 below and in other methods described herein, it may refer to processing pre-processed image data and/or to processing un-pre-processed image data.

At block 206, in some embodiments, the system may process the image data using a first classification network to generate first classification output data indicating a determined surgical specialty type represented by the image data of the surgical environment. In some embodiments, said processing may be carried out by image analysis system 104. The first classification network may be a classification network configured to discriminate between images of surgical environments to determine what surgical specialty type is depicted in different images.

In some embodiments, the first classification network may be a deep neural network, a convolutional neural network, or the like. In some embodiments, the first classification network may be generated (e.g., trained) using a set of training data, such as training image data provided by training/validation image data source 108. In some embodiments, the first classification network may be validated using a set of validation data, such as validation image data provided by training/validation image data source 108. In some embodiments, training image data and/or validation image data used to generate (e.g., train) and validate the first classification network may be labeled image data depicting surgical environments. (In some embodiments, unlabeled image data may alternately or additionally be used to train one or more classification networks.) In some embodiments, labels for the training and/or validation data may comprise labels for surgical specialty type, such that discriminating between the different surgical specialty type labels may train the first classification network to discriminate between images depicting the corresponding different surgical specialty types.

In some embodiments, training data and validation data for the first classification network may be taken from the same initial corpus of image data, such as a data superset of surgical images. In some embodiments, a data superset may be divided (e.g., randomly divided) to form a set of training data and a set of validation data.

In some embodiments, a set of training data and/or a set of validation data used to train/validate the first classification network may be the same set that is used to train/validate one or more additional classification networks (e.g., other classification networks discussed herein, including those used elsewhere in this method). In some embodiments, a set of training data and/or a set of validation data may comprise multiple sets of labels for a single image; e.g., labels denoting a surgical specialty type, labels denoting a procedure type, and/or labels denoting a procedure step for a single image. In some embodiments, different labels for a single image may be used to train/validate different classification networks configured to discriminate with respect to different image categories (e.g., surgical specialty type, procedure type, and procedure step).

In some embodiments, a set of training data and/or a set of validation data used to train/validate the first classification network may be a different set than one that is used to train/validate one or more additional classification networks (e.g., other classification networks discussed herein, including those used elsewhere in this method). In some embodiments, different data sets used to train/validate different classification networks may be wholly non-overlapping, in that they may contain no common data (e.g., no common images). In some embodiments, different data sets used to train/validate different classification networks may be partially overlapping, in that they may contain some common data (e.g., one or more common images) with each set containing some unique data (e.g., at least on unique image per set). In some embodiments, different data sets used to train/validate different classification networks may be wholly overlapping, in that one set may fully encompass another set that is a subset thereof; for example, in some embodiments a first set may correspond to images for a particular surgical specialty type, and a second set may correspond to images for a particular surgical procedure type included therein.

In some embodiments, the first classification network may be a neural network comprising a plurality of layers through which input image data is processed. In some embodiments, the first classification network may comprise a plurality of convolution layers and a plurality of fully-connected layers; in some embodiments, the convolution layers may be positioned earlier in the network such that input image data is first processed through the convolution layers and is thereafter processed through the fully-connected layers.

In some embodiments, the convolution layers of the first classification network may be configured (e.g., trained) without reference to any surgical image training data (e.g., without reference to the training data provided by training/validation image data source 108). Rather, in some embodiments, the convolution layers, along with an initial set of fully-connected layers, may be trained (and/or validated) with respect to an initial set of training/validation image data that is not surgical image data. This initial training/validation process may produce an initial classification network that is not applicable to surgical images, but that may be modified to be applicable to surgical images as described herein. Once the initial classification network is trained (and in some embodiments validated) using the non-surgical training data, the initial classification network may be modified in some embodiments by replacing the fully-connected layers of the network with a new set of fully connected layers configured for use with surgical image data, and the modified initial classification network may be retrained with the new fully-connected layers to generate the first classification network configured to discriminate between surgical images in accordance with the surgical training data (e.g., surgical image training data provided by training/validation image data source 108).

In some embodiments, the first classification network may be generated by modifying a preexisting convolutional neural network such as AlexNet, which is a CNN trained on over 1 million images to classify images into 1000 different categories. In accordance with the modification techniques explained above, AlexNet may be re-trained to transfer the learning for any new image type classification. In some embodiments, AlexNet may be modified by trimming off the final three layers of the AlexNet network and retraining the final three layers with a surgical image training data set.

In some embodiments, generating the first classification network in this manner (e.g., modifying an initial classification network) may allow for preconfigured initial classification networks to be used to accelerate the process for building the first classification network, and may allow for the first classification network to be built with a smaller set of surgical images to be used for training/validation. In some embodiments, generating the first classification network in this manner may allow for the first classification network to be validated for sufficiently accurate performance more quickly than if the first classification network were built from scratch using only a dedicated surgical image training data set.

In some embodiments, the first classification network may be selected and/or retrieved by the system from a set of available classification networks. For example, image analysis system 104 may select the first classification network from a set of classification networks provided by (or via) classification network source 106. In some embodiments, the system may select and/or retrieve the first classification network in accordance with one or more logic rules, including in accordance with one or more determinations made based on analysis of one or more characteristics of the input image data. In some embodiments, the system may select and/or retrieve the first classification network in accordance with user input indicating that the first classification network is the one that should be selected and/or retrieved.

In some embodiments, the first classification network may be configured to process image data as input and to generate, based on the input image data, classification output data, wherein the classification output data may indicate a surgical specialty type represented by the input image data. In some embodiments, the classification output data may indicate a confidence score indicating a level of confidence/certainty by which the first classification network has determined that the input image depicts the determined surgical specialty type. (In some embodiments, determinations as to whether and/or how to change an activation state of a surgical device may be dependent on a confidence score of classification output data, such as by requiring that the confidence score exceed a predetermined confidence threshold before changing the activation state.)

In some embodiments, the system may be configured to store and/or transmit the generated classification output data. For example, the classification output data may be stored locally, may be transmitted for remote and/or distributed storage, or may be transmitted to one or more other system components (e.g., output device 110 and/or surgical device 112) for further use, for example as described below. Furthermore, as described below, the classification output data may be used by image analysis system 104 to make one or more determinations regarding additional classification networks to call and/or apply, one or more output indications to be generated (e.g., by output device 110), and/or one or more control operations to be applied to one or more surgical devices (e.g. surgical device 112).

At block 208, in some embodiments, the system may, in accordance with the first classification output data indicating the determined surgical specialty type, select a second classification network from a first plurality of classification networks. In some embodiments, image analysis system 104 may apply one or more rules or algorithms to select the second classification network based on the first classification output data. In some embodiments, the first plurality of classification networks from which image analysis system 104 chooses may be provided by classification network source 106.

In some embodiments, the system may select the second classification network to further parse the input image data based on a classification identified by the first classification output data. For example, image analysis system 104 may select, as the second classification network, a classification network that is configured to discriminate amongst different surgical procedure types that fall within the surgical specialty type indicated by the first classification output data.

In some embodiments, the second classification network may share any one or more characteristics in common with the first classification network as described above. In some embodiments, while the first classification network may be configured to discriminate between images showing different surgical specialty types, the second classification network may be configured to discriminate between images showing different surgical procedure types. In some embodiments, the second classification network may be configured specifically to discriminate between images showing different surgical procedure types, wherein the input images for the second classification network are images of the surgical specialty type previously identified by the first classification network.

At block 210, in some embodiments, the system may process the image data using the second classification network to generate second classification output data indicating a determined procedure type represented by the image data of the surgical environment. In some embodiments, said processing may be carried out by image analysis system 104.

In some embodiments, the second classification network may be configured to process image data as input and to generate, based on the input image data, classification output data, wherein the classification output data may indicate a surgical procedure type represented by the input image data. In some embodiments, the classification output data may indicate a confidence score indicating a level of confidence/certainty by which the second classification network has determined that the input image depicts the determined surgical procedure type. (In some embodiments, determinations as to whether and/or how to change an activation state of a surgical device may be dependent on a confidence score of classification output data, such as by requiring that the confidence score exceed a predetermined confidence threshold before changing the activation state.)

In some embodiments, the system may be configured to store and/or transmit the generated classification output data. For example, the classification output data may be stored locally, may be transmitted for remote and/or distributed storage, or may be transmitted to one or more other system components (e.g., output device 110 and/or surgical device 112) for further use, for example as described below. Furthermore, as described below, the classification output data may be used by image analysis system 104 to make one or more determinations regarding additional classification networks to call and/or apply, one or more output indications to be generated (e.g., by output device 110), and/or one or more control operations to be applied to one or more surgical devices (e.g. surgical device 112).

In some embodiments, application of the second classification network at block 210 may share any one or more characteristics in common with application of the first classification network at block 206.

At block 212, in some embodiments, the system may, in accordance with the second classification output data indicating the determined procedure type, select a third classification network from a second plurality of classification networks. In some embodiments, image analysis system 104 may apply one or more rules or algorithms to select the third classification network based on the second classification output data. In some embodiments, the second plurality of classification networks from which image analysis system 104 chooses may be provided by classification network source 106.

In some embodiments, the system may select the third classification network to further parse the input image data based on a classification identified by the first and/or second classification output data. For example, image analysis system 104 may select, as the third classification network, a classification network that is configured to discriminate amongst different surgical steps that fall within the surgical procedure type indicated by the second classification output data.

In some embodiments, the third classification network may share any one or more characteristics in common with the first and/or second classification network as described above. In some embodiments, while the first classification network may be configured to discriminate between images showing different surgical specialty types, and while the second classification network may be configured to discriminate between images showing different surgical procedure types, the third classification network may be configured to discriminate between images showing different surgical procedure steps. In some embodiments, the third classification network may be configured specifically to discriminate between images showing different surgical procedure steps, wherein the input images for the third classification network are images of the surgical procedure type previously identified by the second classification network.

In some embodiments, selection of the third classification network at block 212 may share any one or more characteristics in common with selection of the second classification network at block 208.

At block 214, in some embodiments, the system may process the image data using the third classification network to generate third classification output data indicating a determined procedure step represented by the image data of the surgical environment. In some embodiments, said processing may be carried out by image analysis system 104.

In some embodiments, the third classification network may be configured to process image data as input and to generate, based on the input image data, classification output data, wherein the classification output data may indicate a surgical procedure step represented by the input image data. In some embodiments, the classification output data may indicate a confidence score indicating a level of confidence/certainty by which the third classification network has determined that the input image depicts the determined surgical procedure step. (In some embodiments, determinations as to whether and/or how to change an activation state of a surgical device may be dependent on a confidence score of classification output data, such as by requiring that the confidence score exceed a predetermined confidence threshold before changing the activation state.)

In some embodiments, the system may be configured to store and/or transmit the generated classification output data. For example, the classification output data may be stored locally, may be transmitted for remote and/or distributed storage, or may be transmitted to one or more other system components (e.g., output device 110 and/or surgical device 112) for further use, for example as described below. Furthermore, in some embodiments, the classification output data may be used by image analysis system 104 to make one or more determinations regarding additional classification networks to call and/or apply, one or more output indications to be generated (e.g., by output device 110), and/or one or more control operations to be applied to one or more surgical devices (e.g. surgical device 112).

In some embodiments, application of the third classification network at block 214 may share any one or more characteristics in common with application of the second classification network at block 210 and/or application of the first classification network at block 206.

In some embodiments, block 216 may follow from any one or more of blocks 206, 210, and 214. At block 216, in some embodiments, the system may, based on one or more of the classification outputs, provide an output indication. In some embodiments, the output indication may be any visible, audible, haptic, and/or otherwise perceptible indication and/or signal produced in accordance with one or more of the classification outputs and configured to convey information associated with the one or more classification outputs. In some embodiments, the output indication may be a visually displayed indication (e.g., displayed on the display), a visual indication such as an LED indication, an audible indication such as one or more words or sounds produced by a speaker, and/or a haptic indication such as one or more vibrations and/or pulses produced by a haptic output device.

In the example of system 100 of FIG. 1, the one or more classification output indications may be provided by output device 110, which may receive an electronic transmission (e.g., via any wired or wireless electronic communication medium, including by any suitable network communication protocol) including the one or more classification outputs. Output device 110 may then generate and provide the output indication(s) on the basis of the received classification output(s). In some embodiments, output device 110 may comprise a display, an indicator light (e.g., LED), a speaker, a haptic output device, or the like.

In some embodiments, block 218 may follow from any one or more of blocks 206, 210, and 214. At block 218, in some embodiments, the system may, based on one or more of the classification outputs, automatically change an activation state of a surgical device. In the example of system 100 in FIG. 1, the system may change an activation state of surgical device 112 by transmitting one or more control signals to surgical device 112 from image analysis system 104 (or, alternately or additionally, surgical device 112 may change an activation state of itself in response to receiving a transmission of one or more classification outputs from image analysis system 104). In some embodiments, transmissions of classification outputs and/or control signals from image analysis system 104 to surgical device 112 may be made via any wired or wireless electronic communication medium, including by any suitable network communication protocol.

In some embodiments, the system may make one or more determinations as to whether to change an activation state of a surgical device such as surgical device 112 in accordance with one or more output classifications determined by the device. For example, system 100 may apply one or more rules in order to determine whether to change an activation state of surgical device 112 based on the one or more output classifications that have been determined by image analysis system 104 by applying the first, second, and/or third classification network. In some embodiments, system 100 may apply one or more rules to configure surgical device in accordance with one or more predefined activation states that are associated with a surgical specialty type, surgical procedure type, or procedure step determined by system 100. In this way, system 100 may automatically configure one or more settings of surgical device 112 to optimize surgical device 112 for the surgical environment based on the input image data.

In some embodiments, the one or more surgical devices may include any of the one or more surgical devices discussed elsewhere herein, including one or more illumination and/or image capture devices. In some embodiments, a surgical device may comprise an indicator device configured to indicate to a human operator that one or more other surgical devices should be activated and/or deactivated.

In some embodiments, changing an activation state may comprise changing a device from inactive (e.g., off) to active (e.g., on) or changing a device from active (e.g., on) to inactive (e.g., off). In some embodiments, changing an activation state may comprise changing a setting or configuration of a device without changing the device from off to on or from on to off.

In some embodiments, the system may be configured to change an activation state of a surgical device in accordance with an identified surgical specialty type, surgical procedure type, and/or procedure step. In some embodiments, the system may be configured to change an activation state of a surgical device in accordance with one or more confidence scores associated with an identified surgical specialty type, surgical procedure type, and/or procedure step. In some embodiments, the system may be configured to change an activation state if a confidence score exceeds (or, alternately, does not exceed) one or more predefined threshold confidence levels. In some embodiments, changing an activation state of the one or more surgical devices may be performed on the basis of one or more additional trigger conditions also being satisfied. In some embodiments, changing an activation state of a surgical device may be performed on the basis of one or more trigger conditions associated with the one or more classification outputs, as shown at block 218.

In some embodiments, changing an activation state of a surgical device may be automatically performed on the basis alone of one or more trigger conditions being met for a single frame of surgical image from a surgical video feed. In some embodiments, one or more trigger conditions (including those recited herein) may be required to be met for a certain consecutive number of frames analyzed (e.g., in a surgical video feed) before changing an activation state. In some embodiments, an activation state may be prevented from being changed, despite one or more trigger conditions being met, during a predefined or dynamically determined period of time, such as for a predefined period of time after the activation state was previously changed.

Figure 3:
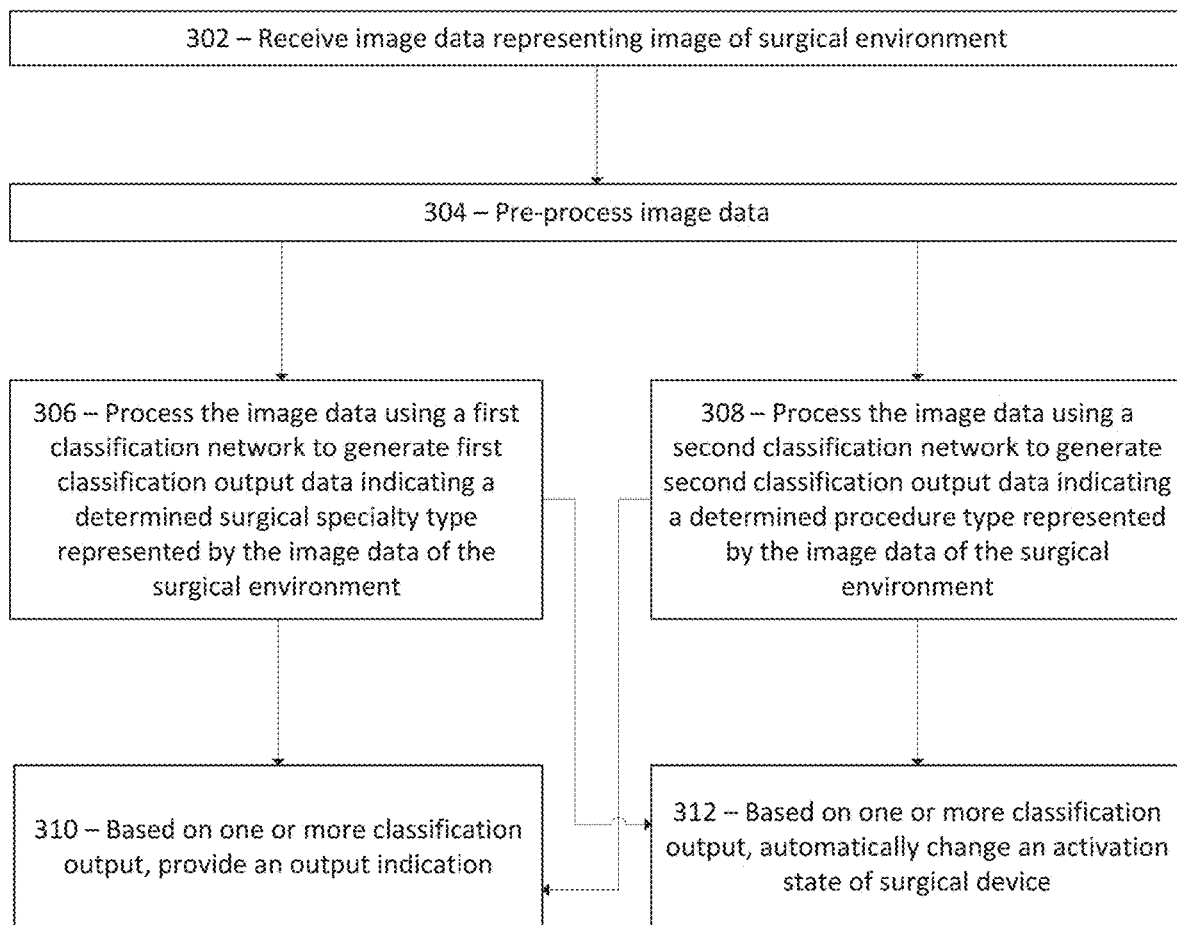
FIG. 3 depicts a flowchart representing an exemplary method for automatic detection of surgical specialty type and procedure type, in accordance with some embodiments.

FIG. 3 depicts a flowchart representing an exemplary method for automatic detection of surgical specialty type and procedure type, in accordance with some embodiments.

As described below in detail, method 300 may enable an image analysis system to receive surgical images or videos; to process the surgical images or videos to determine a surgical specialty type, procedure type, and/or procedure step depicted in the received images/videos; and to provide an output and/or automatically enable, disable, or configure a setting of one or more surgical devices based on the determined surgical specialty type, procedure type, and/or procedure step.

As described below, method 300 may enable a system to receive surgical image data and to process the image data using both (1) a first classification network configured to determine a surgical specialty type represented by the image data and (2) a second classification network configured to determine a procedure type represented by the image data. In some embodiments, the system may further apply one or more additional classification networks to the image data, such as a third classification network configured to determine a procedure step represented by the image data. Based on one or more of the determined surgical specialty type, the determined procedure type (and in some embodiments the determined procedure step), the system may then provide one or more output indications and/or may automatically change an activation state of a surgical device.

In some embodiments, method 300 (including its various steps and components) may share any one or more characteristics in common with method 200 (including its corresponding various steps and components) as explained above. In some embodiments, method 300 may differ from method 200 in that method 200 may be configured to apply various classification networks in series, such as by first applying a first classification network and responsively determining on the basis of the outcome which classification network(s) to subsequently apply. Method 300, on the other hand, may be configured to apply various classification networks in parallel, such as by applying a first classification network and a second classification network (configured to discriminate among different categories) to the same input data, independently of one another (and in some embodiments at the same time). In some embodiments, there may be no causal or dependent link between the application of a first classification network and the application of a second classification network in method 300, and the output data generated by one or both independent applications may be used to provide an output indication and/or to automatically change an activation state of a surgical device.

In some embodiments, method 300 may be carried out, in whole or in part, by one or more of the components of a system for automatic detection of surgical specialty type and procedure type, such as system 100 described above with respect to FIG. 1. In some embodiments, any one or more of the aspects of method 300 may be combined, in whole or in part, with any one or more of the aspects of FIG. 1, and/or with any one or more of the systems, methods, devices, and/or techniques described elsewhere herein.

In some embodiments, at block 302, the system may receive image data representing an image of a surgical environment. Receipt of image data at block 302 may share any one or more characteristics in common with receipt of image data at block 202 in method 200 as described above.

In some embodiments, at block 304, the system may perform one or more pre-processing techniques on the received image data. Performance of one or more pre-processing techniques at block 304 may share any one or more characteristics in common with performance of one or more pre-processing techniques at block 204 in method 200 as described above.

In some embodiments, at block 306, the system may process the image data using a first classification network to generate first classification output data indicating a determined surgical specialty type represented by the image data of the surgical environment. Processing the image data using the first classification network at block 306 may share any one or more characteristics in common with processing the image data using the first classification network at block 206 in method 200 as described above. In some embodiments, while the first classification network selected at block 206 may be a "top level" classification network configured to discriminate between a broader set of categories (e.g., surgical specialty type) than the category of a classification network applied later in method 200 (e.g., surgical procedure type), the first classification network selected at block 306 may be a classification network configured to make any discrimination and may be selected without regard for any prior or subsequent classification network processing in method 300.

As described above at block 206, the first classification network at block 306 may be configured to process image data as input and to generate, based on the input image data, classification output data, wherein the classification output data may indicate a surgical specialty type represented by the input image data (including in some embodiments a confidence score). In some embodiments, the system may be configured to store and/or transmit the generated classification output data in a similar manner (and for similar uses) as described above with respect to block 206 of method 200.

In some embodiments, at block 308, the system may process the image data using a second classification network to generate second classification output data indicating a determined procedure type represented by the image data of the surgical environment. Processing the image data using the second classification network at block 308 may share any one or more characteristics in common with processing the image data using the second classification network at block 210 in method 200 as described above. In some embodiments, while the second classification network selected at block 210 may be a "lower level" classification network configured to discriminate between a narrower set of categories (e.g., surgical procedure type) than the category of a classification network applied earlier in method 200 (e.g., surgical specialty type), the second classification network selected at block 308 may be a classification network configured to make any discrimination and may be selected without regard for any prior or subsequent classification network processing in method 300.

As described above at block 210, the second classification network at block 308 may be configured to process image data as input and to generate, based on the input image data, classification output data, wherein the classification output data may indicate a surgical procedure type represented by the input image data (including in some embodiments a confidence score). In some embodiments, the system may be configured to store and/or transmit the generated classification output data in a similar manner (and for similar uses) as described above with respect to block 206 of method 200.

In some embodiments, the second classification network applied at block 308 may be the same as the second classification network applied at block 210. In some embodiments, the second classification network applied at block 308 may differ from the second classification network applied at block 210; for example, the second classification network applied at block 210 may be configured specifically to discriminate between images showing different surgical procedure types, wherein the input images for the second classification network are images of a specific surgical specialty type (e.g., the procedure type previously identified in method 200), whereas the second classification network applied at block 308 may be configured to identify different surgical procedure types based on images showing various different surgical specialty types. In some embodiments, the second classification network applied at block 210 may be trained using a training dataset including only images of a single surgical specialty type, while the second classification network applied at block 308 may be trained using a training dataset including images of multiple different surgical specialty types.

In some embodiments, application of different classification networks at blocks 306 and 308 to the same input data may share any one or more characteristics in common with one another. In some embodiments, a difference between blocks 306 and 308 may be that the two different classification networks applied are configured to classify the input image into different kinds of categories, including overlapping categories (e.g., surgical specialty type and procedure type) or non-overlapping categories. In some embodiments, method 300 may include applying one or more additional classification networks to the same input data in parallel with blocks 306 and 308, such as a third classification network configured to categorize images according to procedure step.

In some embodiments, block 310 may follow from any one or more of blocks 306 and 308. In some embodiments, at block 310, the system may, based on one or more of the classification outputs, provide an output indication. Providing an output indication based on one or more classification outputs at block 310 may share any one or more characteristics in common with providing an output indication based on one or more classification outputs at block 216 in method 200 as described above. In some embodiments, the output indication provided at block 310 may be based on one or more additional classification outputs in addition to the first classification output and the second classification output.

In some embodiments, block 312 may follow from any one or more of blocks 306 and 308. In some embodiments, at block 312, the system may, based on one or more classification outputs, automatically change an activation state of a surgical device. Automatically changing an activation state of a surgical device at block 312 may share any one or more characteristics in common with automatically changing an activation state of a surgical device at block 218 in method 200 as described above. In some embodiments, automatically changing an activation state of a surgical device at block 312 may be based on one or more additional classification outputs in addition to the first classification output and the second classification output.

Figure 4:
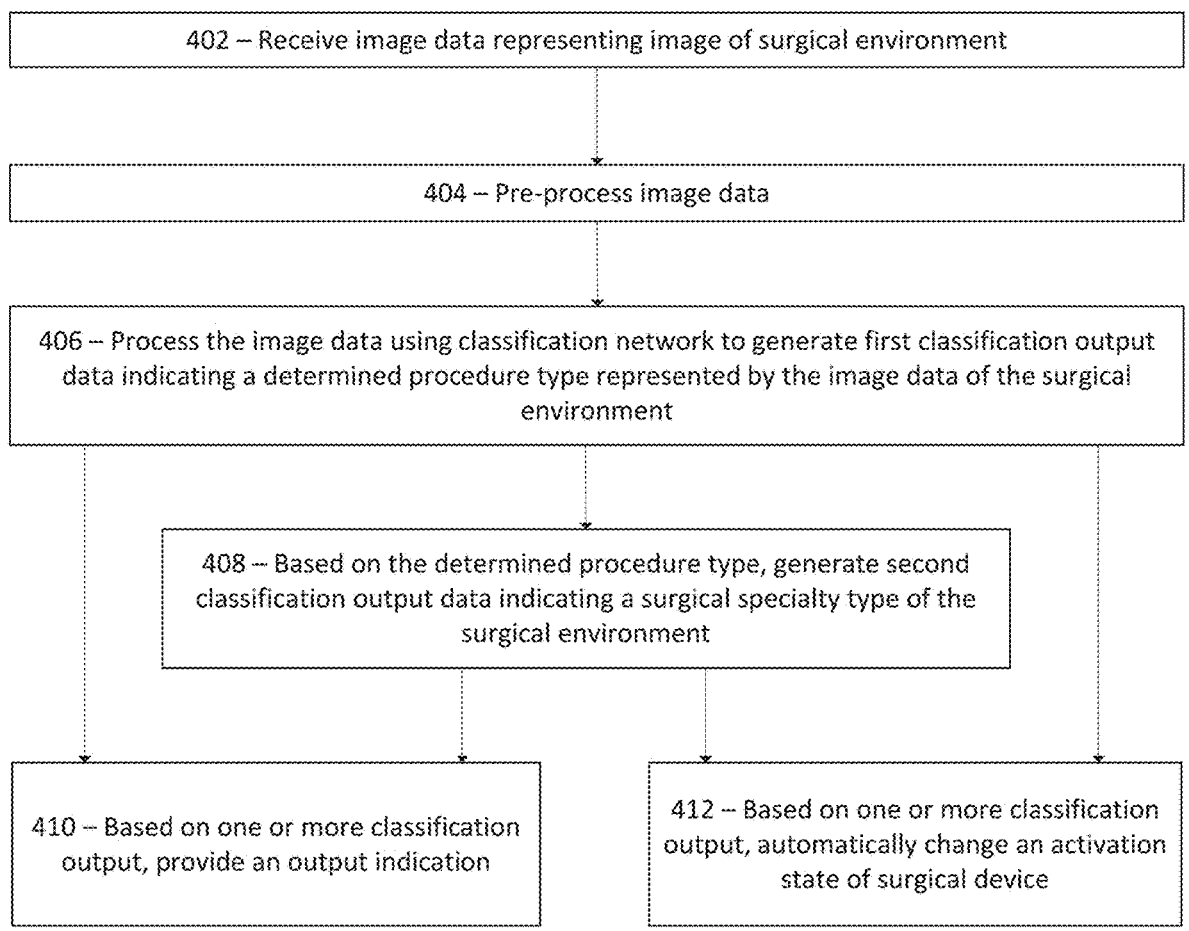
FIG. 4 depicts a flowchart representing an exemplary method for automatic detection of surgical specialty type and procedure type, in accordance with some embodiments.

FIG. 4 depicts a flowchart representing an exemplary method for automatic detection of surgical specialty type and procedure type, in accordance with some embodiments.

As described below in detail, method 400 may enable an image analysis system to receive surgical images or videos; to process the surgical images or videos to determine a surgical specialty type, procedure type, and/or procedure step depicted in the received images/videos; and to provide an output and/or automatically enable, disable, or configure a setting of one or more surgical devices based on the determined surgical specialty type, procedure type, and/or procedure step.

As described below, method 400 may enable a system to receive surgical image data and to process the image data using a classification network configured to determine a surgical procedure type represented by the image data, and to subsequently determine, based on the determined surgical procedure type, a corresponding surgical specialty type represented by the input data. In some embodiments, the system may determine the procedure type using the classification network, and may then determine the corresponding surgical specialty type that encompasses the surgical procedure type by referring to a lookup table, index, or the like. In some alternate embodiments, the system may apply a classification network to input data to determine a different kind of classification, such as a procedure step, and then may determine other broader classifications for the image data (such as procedure type and/or surgical specialty type) on the basis of that procedure-step determination. Based on one or both of the determined surgical specialty type and the determined procedure type (and/or, in some embodiments, the determined procedure step), the system may then provide one or more output indications and/or may automatically change an activation state of a surgical device.

In some embodiments, method 400 (including its various steps and components) may share any one or more characteristics in common with method 200 (including its corresponding various steps and components) as explained above and/or with method 300 (including its corresponding various steps and components) as explained above. In some embodiments, method 400 may differ from method 200 and method 300 in that methods 200 and 300 may be configured to determine a surgical specialty type and a surgical procedure type (or, more generally two classification outputs for input data) by using two different classification networks. Method 400, on the other hand, may be configured to apply a single classification network to generate a single classification output indicating a classification/categorization of the input data, and to subsequently determine/infer a second classification/categorization of the input data based on the single classification output. In the example shown, method 400 may determine a surgical procedure type using a classification network, and may then determine, based on the surgical procedure type identified, a corresponding surgical specialty type.

In some embodiments, method 400 may be carried out, in whole or in part, by one or more of the components of a system for automatic detection of surgical specialty type and procedure type, such as system 100 described above with respect to FIG. 1. In some embodiments, any one or more of the aspects of method 400 may be combined, in whole or in part, with any one or more of the aspects of FIG. 1, and/or with any one or more of the systems, methods, devices, and/or techniques described elsewhere herein.

In some embodiments, at block 402, the system may receive image data representing an image of a surgical environment. Receipt of image data at block 402 may share any one or more characteristics in common with receipt of image data at block 202 in method 200 as described above and/or at block 302 in method 300 as described above.

In some embodiments, at block 404, the system may perform one or more pre-processing techniques on the received image data. Performance of one or more pre-processing techniques at block 404 may share any one or more characteristics in common with performance of one or more pre-processing techniques at block 204 in method 200 as described above and/or at block 304 in method 300 as described above.

In some embodiments, at block 406, the system may process the image data using a classification network to generate first classification output data indicating a determined procedure type represented by the image data of the surgical environment. Processing the image data using the classification network at block 304 may share any one or more characteristics in common with processing the image data using the second classification network at block 210 in method 200 as described above and/or with processing the image data using the second classification network at block 308 in method 300 as described above. In some embodiments, the classification network selected at block 406 may be any "lower level" classification network configured to discriminate between a narrower set of categories (e.g., surgical procedure type) than a broader categories type to be determined later in method 400 (e.g., surgical specialty type).

As described above at block 210 and/or above at block 308, the classification network at block 406 may be configured to process image data as input and to generate, based on the input image data, classification output data, wherein the classification output data may indicate a surgical procedure type represented by the input image data (including in some embodiments a confidence score). In some embodiments, the system may be configured to store and/or transmit the generated classification output data in a similar manner (and for similar uses) as described above with respect to block 206 of method 200. In some embodiments, as described below, the classification output data may be stored and/or transmitted for later use in inferring or otherwise determining an additional classification for the input data, such as a broader category classification such as a surgical specialty type.

In some embodiments, at block 408, the system may, based on the determined procedure type, generate second classification output data indicating a surgical specialty type of the surgical environment. In some embodiments, rather than generating the second classification output data using a second classification network, the system may generate the second classification output data using one or more lookup tables, indexes, databases, or the like to access stored data regarding a broader categorization that corresponds to the narrower categorization indicated by the first classification output data. For example, when the first classification output data indicates a surgical procedure type, the system may look up a corresponding surgical specialty type to which that surgical procedure type corresponds. When the first classification output data indicates a surgical procedure step, the system may look up a corresponding surgical procedure type and/or surgical specialty type to which that surgical procedure step corresponds. The second classification output may be generated to indicate the broader categorization that was looked up.

In some embodiments, the second classification output may have no confidence score. In some embodiments, the second classification output may have a highest possible confidence score (e.g., 100%). In some embodiments, the second classification output may have a confidence score determined in accordance with (e.g., matching, or otherwise algorithmically determined based on) a confidence score of the first classification output.

In some embodiments, block 410 may follow from any one or more of blocks 406 and 408. In some embodiments, at block 410, the system may, based on one or more of the classification outputs, provide an output indication. Providing an output indication based on one or more classification outputs at block 410 may share any one or more characteristics in common with providing an output indication based on one or more classification outputs at block 216 in method 200 as described above and/or at block 310 in method 300 as described above. In some embodiments, the output indication provided at block 410 may be based on one or more additional classification outputs in addition to the first classification output and the second classification output.

In some embodiments, block 412 may follow from any one or more of blocks 406 and 408. In some embodiments, at block 412, the system may, based on one or more classification outputs, automatically change an activation state of a surgical device. Automatically changing an activation state of a surgical device at block 412 may share any one or more characteristics in common with automatically changing an activation state of a surgical device at block 218 in method 200 as described above and/or at block 312 in method 300 as described above. In some embodiments, automatically changing an activation state of a surgical device at block 312 may be based on one or more additional classification outputs in addition to the first classification output and the second classification output.

Figure 5:
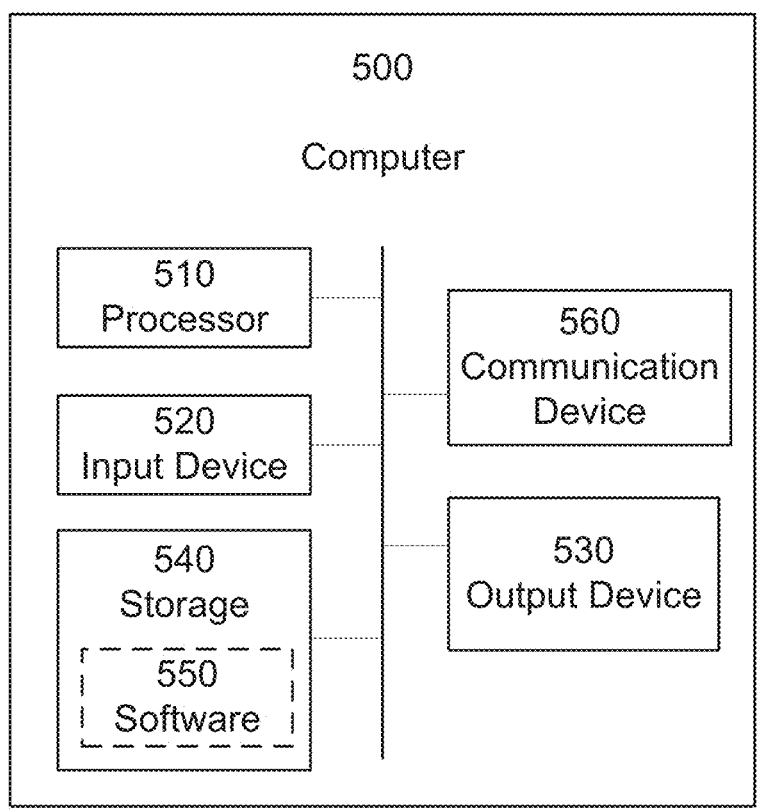
FIG. 5 depicts a computer, in accordance with some embodiments.

FIG. 5 illustrates a computer, in accordance with some embodiments. Computer 500 can be a component of a system for automatic detection of surgical specialty type and procedure type, such as system 100 and/or any of its subcomponents described above with respect to FIG. 1. In some embodiments, computer 500 may be configured to execute a method for automatic detection of surgical specialty type and procedure type, such as all or part of any one or more of methods 200, 300, and 400 described above with respect to FIGS. 2-4.

Computer 500 can be a host computer connected to a network. Computer 500 can be a client computer or a server. As shown in FIG. 5, computer 500 can be any suitable type of microprocessor-based device, such as a personal computer; workstation; server; or handheld computing device, such as a phone or tablet. The computer can include, for example, one or more of processor 310, input device 520, output device 530, storage 540, and communication device 560.

Input device 520 can be any suitable device that provides input, such as a touch screen or monitor, keyboard, mouse, or voice-recognition device. Output device 530 can be any suitable device that provides output, such as a touch screen, monitor, printer, disk drive, or speaker.

Storage 540 can be any suitable device that provides storage, such as an electrical, magnetic, or optical memory, including a RAM, cache, hard drive, CD-ROM drive, tape drive, or removable storage disk. Communication device 560 can include any suitable device capable of transmitting and receiving signals over a network, such as a network interface chip or card. The components of the computer can be connected in any suitable manner, such as via a physical bus or wirelessly. Storage 540 can be a non-transitory computer-readable storage medium comprising one or more programs, which, when executed by one or more processors, such as processor 510, cause the one or more processors to execute methods described herein, such as all or part of any one or more of methods 200, 300, and 400 described above with respect to FIGS. 2-4.

Software 550, which can be stored in storage 540 and executed by processor 510, can include, for example, the programming that embodies the functionality of the present disclosure (e.g., as embodied in the systems, computers, servers, and/or devices as described above). In some embodiments, software 550 can be implemented and executed on a combination of servers such as application servers and database servers.

Software 550 can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 540, that can contain or store programming for use by or in connection with an instruction execution system, apparatus, or device.

Software 550 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include, but is not limited to, an electronic, magnetic, optical, electromagnetic, or infrared wired or wireless propagation medium.

Computer 500 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 500 can implement any operating system suitable for operating on the network. Software 550 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A surgical system, the system comprising:
one or more processors and memory storing instructions that, when executed by the one or more processors, cause the system to:
receive image data representing a surgical environment;
process the image data using a first classification network to generate first classification output data indicating a determined surgical specialty type represented by the image data of the surgical environment, wherein the determined surgical specialty is a class of procedures;
in accordance with the first classification output data indicating the determined surgical specialty type, select a second classification network from a first plurality of classification networks; and process the image data using the second classification network to generate second classification output data indicating a determined procedure type represented by the image data of the surgical environment, wherein procedure type is of narrower classification than surgical specialty type.

2. The system of claim 1, wherein:
the first classification network is trained using a first set of training image data; and
the second classification network is trained using a second set of training image data.

3. The system of claim 2, wherein the second set of training image data is a subset of the first set of training image data.

4. The system of claim 1, wherein the first classification network and the second classification network are both trained using a same set of training image data.

5. The system of claim 1, wherein one or more of the first classification network and the second classification network comprises a convolutional neural network comprising a plurality of convolution layers and a plurality of fully-connected layers.

6. The system of claim 5, wherein:
the fully-connected layers are configured in accordance with a set of training image data comprising surgical images labeled with one or both of surgical specialty type metadata and procedure type metadata; and
the convolution layers are configured without reference to the set of training image data.

7. The system of claim 1, wherein the one or more processors are further configured to:
in accordance with the second classification output data indicating the determined procedure type, select a third classification network from a second plurality of classification networks; and
process the image data using the third classification network to generate third classification output data indicating a determined procedure step represented by the image data of the surgical environment.

8. The system of claim 1, further comprising an output device, wherein the one or more processors are further configured to:
based on one or more of the first classification output data and the second classification output data, automatically provide an output indication via the output device.

9. The system of claim 8, wherein the output device comprises a display and providing an output indication comprises displaying the output indication.

10. The system of claim 1, wherein receiving the image data comprises receiving the image data from an endoscopic video feed.

11. The system of claim 1, wherein the one or more processors are further configured to pre-process the image data to configure the image data to be processed by one or more of the first classification network and the second classification network.

12. The system of claim 11, wherein pre-processing the image data comprises cropping the image data.

13. The system of claim 11, wherein pre-processing the image data comprises scaling the image data.

14. The system of claim 11, wherein pre-processing the image data comprises one or more of translating, flipping, shearing, and stretching the image data.

15. The system of claim 1, wherein selecting the second classification network comprises selecting the second classification network based on a determination that the second classification network is configured to discriminate between different procedure types that fall within the determined surgical specialty type.

16. The system of claim 1, wherein selecting the second classification network comprises applying one or more rules or algorithms to select the second classification network.

17. The system of claim 1, wherein the first plurality of classification networks from which the second classification network is selected are provided by a classification network source.

18. The system of claim 17, wherein the classification network source is configured to transmit classification network data to the one or more processors, wherein the classification network data comprises one or more data types selected from the group comprising: classification network metadata and one or more rules regarding applying the one or more classification networks.

19. A method configured to be performed by a surgical system comprising one or more processors, the method comprising:
receiving image data representing a surgical environment;
processing the image data using a first classification network to generate first classification output data indicating a determined surgical specialty type represented by the image data of the surgical environment, wherein the determined surgical specialty is a class of procedures;
in accordance with the first classification output data indicating the determined surgical specialty type, selecting a second classification network from a first plurality of classification networks; and
processing the image data using the second classification network to generate second classification output data indicating a determined procedure type represented by the image data of the surgical environment, wherein procedure type is of narrower classification than surgical specialty type.

20. A non-transitory computer-readable storage medium storing instructions configured to be executed by one or more processors of a surgical system to cause the surgical system to:
receive image data representing a surgical environment;
process the image data using a first classification network to generate first classification output data indicating a determined surgical specialty type represented by the image data of the surgical environment, wherein the determined surgical specialty is a class of procedures;
in accordance with the first classification output data indicating the determined surgical specialty type, select a second classification network from a first plurality of classification networks; and
process the image data using the second classification network to generate second classification output data indicating a determined procedure type represented by the image data of the surgical environment, wherein procedure type is of narrower classification than surgical specialty type.

* * * * *